United States Patent [19]
Pinke et al.

[11] 3,977,987
[45] Aug. 31, 1976

[54] FUEL AND LUBRICANT COMPOSITIONS CONTAINING NOVEL PYRROLIDINYL OR PIPERIDINYL-SUBSTITUTED DIPHENYL ALKANE ANTIOXIDANTS

[75] Inventors: Paul A. Pinke, Des Plaines; Stephen N. Massie, Palatine, both of Ill.

[73] Assignee: Universal Oil Products Company, Des Plaines, Ill.

[22] Filed: Nov. 4, 1975

[21] Appl. No.: 520,579

Related U.S. Application Data

[63] Continuation-in-part of Ser. No. 339,818, March 9, 1973, Pat. No. 3,853,887.

[52] U.S. Cl. ................................ 252/50; 44/63; 44/74; 252/401
[51] Int. Cl.$^2$ .................................... C10M 1/32
[58] Field of Search ................ 252/50, 401; 44/63, 44/74

[56] References Cited
UNITED STATES PATENTS

| 2,809,164 | 10/1957 | Pruett | 252/50 X |
| 3,011,976 | 12/1961 | Cyba | 252/50 X |
| 3,110,671 | 11/1963 | Cyba | 252/50 |
| 3,216,939 | 11/1965 | Cyba | 252/50 |
| 3,222,285 | 12/1965 | Rai et al. | 252/50 X |
| 3,384,614 | 5/1968 | Rosenwald | 252/401 X |
| 3,755,171 | 8/1973 | Cyba et al. | 252/50 X |

*Primary Examiner*—Delbert E. Gantz
*Assistant Examiner*—Andrew H. Metz
*Attorney, Agent, or Firm*—James R. Hoatson, Jr.; Raymond H. Nelson; William H. Page, II

[57] ABSTRACT

A novel antioxidant utilized in a petroleum substrate comprising mono- or di(heterocyclic nitrogen)-substituted diarylalkanes is disclosed.

12 Claims, No Drawings

FUEL AND LUBRICANT COMPOSITIONS CONTAINING NOVEL PYRROLIDINYL OR PIPERIDINYL-SUBSTITUTED DIPHENYL ALKANE ANTIOXIDANTS

Cross-Reference to Related Applications

This is a continuation-in-part of our copending application Serial No. 339,818, filed March 9, 1973 and now U.S. Pat. No. 3,853,887, all the teachings of which are specifically incorporated herein by reference.

This invention relates to mono- or di(heterocyclic nitrogen)-substituted diarylalkanes. More specifically, this invention relates to a petroleum substrate containing as an antioxidant an effective amount of mono- or di(heterocyclic nitrogen-substituted diarylalkane.

It is well known in the prior art that various nitrogen-containing compounds may be utilized to prevent oxidation. It is also well known in the prior art that antioxidants may be added to petroleum substrates, especially gasoline, to prevent the formation of "gum" which results from the interreaction of the olefinic materials. The most common nitrogen antioxidants known to the art are probably various diamines as exemplified by the following structure:

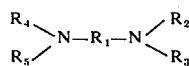

wherein $R_1$, may be phenyl (phenylenediamine) or alkyl (alkylenediamine) and $R_2$, $R_3$, $R_4$ or $R_5$ may be hydrogen, lower alkyl, aryl, lower cycloalkyl, substituted aryl or substituted cycloalkyl.

In contradistinction to the prior art it has now been discovered that mono- or di(heterocyclic nitrogen)-substituted diarylalkanes may be added to petroleum substrates, said diarylalkanes functioning as an antioxidant. The utilization of the mono- or di(heterocyclic nitrogen)-substituted diarylalkanes as antioxidants will also result in a benefit to the gasoline consumer as a consequence of alleviating gasoline shortage problems. The mono- or di(heterocyclic nitrogen)-substituted diarylalkanes will permit a greater bulk of petroleum substrate, particularly gasoline, to be stored over a longer period of time as a result of the prevention of gum formation.

The mono- or di(heterocyclic nitrogen)-substituted diarylalkanes, of the present invention may be utilized as antioxidants in any petroleum substrate. The mono- or di(heterocyclic nitrogen)-substituted diarylalkanes will prevent oxidation over a long period of time, therefore, alleviating any problems of gum or residue formation during storage. Another use of the mono- or di(-heterocyclic nitrogen)-substituted diarylalkanes is to stabilize anti-knock agents in gasoline. A specific example of the utility of the mono- or di-(heterocyclic nitrogen)-substituted diarylalkanes is the use of an effective amount of 4,4-bis-(N-pyrrolidinyl)-diphenylmethane to prevent gum or residue formation in a storage tank of gasoline.

It is therefore an object of this invention to provide an antioxidant for a petroleum substrate.

A further object of this invention is to provide an antioxidant for a petroleum substrate which will possess great antioxidant capabilities and therefore be less expensive on a cost-performance basis.

In one aspect an embodiment of this invention resides in a petroleum substrate containing, as an antioxidant therefore, an effective amount of a mono- or di(-heterocyclic nitrogen)-substituted diarylalkane.

A specific embodiment of this invention resides in the utilization of an effective amount of 4,4'-bis-(N-pyrrolidinyl)diphenylmethane in a gasoline petroleum substrate to prevent the formation of gum.

A second specific embodiment of this invention resides in the utilization of an effective amount of 4-amino-4-(N-pyrrolidinyl)-diphenylmethane in a gasoline petroleum substrate to prevent the formation of gum and to stabilize anti-knock agents.

Other objects and embodiments will be found in the following further detailed description of the present invention.

As hereinbefore set forth the present invention is concerned with a petroleum substrate containing, as an antioxidant therefore, an effective amount of a mono- or di(heterocyclic nitrogen)-substituted diarylalkane. The effective amount of the mono- or di(heterocyclic nitrogen)-substituted diarylalkane will range from about 5ppm to about 200ppm depending on the type of petroleum substrate, the type of antioxidant utilized and the desired stability of the petroleum substrate. It is also contemplated within the scope of this invention that the mono- or di(heterocyclic nitrogen)-substituted diarylalkane be present in excess of 200ppm, although economic considerations usually make such excess concentrations impractical. Examples of mono- or di(-heterocyclic nitrogen)-substituted diarylalkane would include all compounds in accordance with the following structure

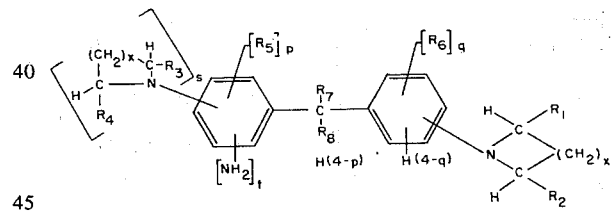

wherein $R_1$, $R_2$, $R_3$, $R_4$, $R_5$, $R_6$, $R_7$ and $R_8$ are selected from a group consisting of methyl or hydrogen, x is selected from the numbers 2 and 3, s is selected from the numbers 0 or 1, t is selected from the numbers 1 or 0 wherein, when s is equal to 0, t is equal to 1 and when s is equal to 1, t is equal to 0, and p and q are selected from the integers from 0 to 4. Specific examples of the structures of the mono- or di-(heterocyclic nitrogen)-substituted diarylalkanes may be exemplified by

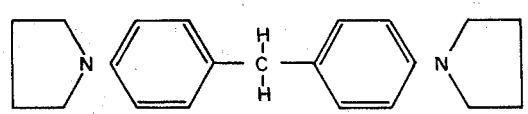

4,4'-bis(N-pyrrolidinyl)diphenylmethane

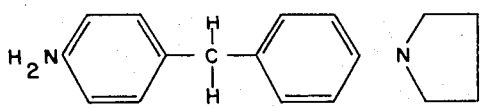

4-amino-4'-(N-pyrrolidinyl)diphenylmethane

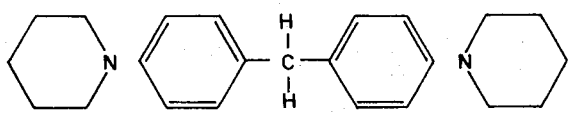

4,4'-bis(N-piperidinyl)diphenylmethane

Other suitable mono- or di(heterocyclic nitrogen)-ubstituted diarylalkanes would include:
4-amino-4'-(N-piperidinyl)diphenylmethane
4-amino-3'-(N-piperidinyl)diphenylmethane
3,3'-bis-(N-pyrrolidinyl)diphenylmethane
4-(N-piperidinyl)-4'-(N-pyrrolidinyl)diphenylmethane
4-amino-3-methyl-4'-(N-piperidinyl)diphenylmethane
4-amino-4-methyl-4'-(N-piperidinyl)diphenylmethane
4-amino-2-methyl-4'-(N-piperidinyl)diphenylmethane
4-amino-2,3-dimethyl-4'-(N-piperidinyl)diphenylmethane
4,4'-bis-(N-piperidinyl)-2-methyldiphenylmethane
2,2-bis[4-(N-pyrrolidinyl)phenyl]propane
1-[2-(N-pyrrolindinylphenyl]-1-[4-(N-pyrrolidinyl)-phenyl]-ethane
2-[4-aminophenyl]-2-[4-(N-pyrrolidinyl)propane
bis[3,5-dimethyl-4-(N-pyrrolidinyl)phenyl]methane In a preferred embodiment of the present invention it is contemplated that the mono- or di(heterocyclic nitrogen)-substituted diarylalkane may be prepared by cycloalkylating a primary amine with a heterocyclic oxygen compound in the presence of a catalyst selected from the group consisting of a hydrogen halide and a metal selected from Group VIII of the Periodic Table on a heterogeneous inorganic support and recovering the resultant mono- or di(heterocyclic nitrogen)-substituted diarylalkanes. The reaction is effected under a reaction condition which includes an elevated temperature in the range of from about 50°C. to about 300°C. and preferably in a range of from about 100°C. to about 200°C. In addition, another reaction condition involves pressure, said pressure ranging from about atmospheric up to about 200 atmospheres or more. When superatmospheric pressurs are employed, said pressure is afforded by the introduction of a substantially inert gas such as nitrogen, helium or argon into the reaction zone, the particular pressure which is used being that which is necessary to maintain a major portion of the reactants in the liquid phase.

The catalytic composition of matter contemplated within the scope of this invention comprises a hydrogen halide or a metal selected from Group VIII of the Periodic Table on a heterogeneous inorganic support. Examples of suitable hydrogen halide catalysts would include hydrochloric acid, hydrogen fluoride, hydrogen bromide, hydrogen iodide, anhydrous hydrochloric acid, anhydrous hydrogen iodide, anhydrous hydrogen bromide, etc. Suitable examples of metals selected from Group VIII of the Periodic Table would include iron, cobalt, nickel, ruthenium, rhodium, palladium, osmium, iridium, platinum, etc. Suitable examples of heterogeneous inorganic oxide supports which may be used for the dispersal of the Group VIII metal would include alumina, silica, magnesia, thoria, zirconia, alumina-silica, alumina-magnesia, alumina-silica-magnesia, magnesia-thoria, silica-magnesia-zirconia or any mixture thereof.

In another preferred embodiment of the present invention, it is found that a catalyst comprising the Group VIII metal on a heterogeneous inorganic support may be enhanced by the addition of a metal selected from Group VIB or Group VIIB of the Periodic Table. Suitable examples of metals which may be selected from Group VIB of the Periodic Table would include chromium, molybdenum and tungsten, while suitable examples of metals which may be selected from Group VIIB of the Periodic Table would include manganese and rhenium.

In yet another preferred embodiment of the present invention, it is found that the catalytic activity of the catalyst comprising a metal selected from Group VIII of the Periodic Table on an inorganic support, coupled with metals selected from Groups VIB or VIIB of the Periodic Table, if so desired, will be magnified by treatment of the heterogeneous inorganic oxide by a haliding agent. Suitable examples of halliding agents would include hydrogen chloride, hydrogen bromide, hydrogen iodide, hydrogen fluoride and thionyl chloride.

It is understood that the aforementioned hydrogen halides, Group VIII metals, Group VIB metals, Group VIIB metals, inorganic oxide supports and haliding agents are only representative of the class of compounds which may be employed and that the present invention is not necessarily limited thereto.

Examples of suitable primary amines which may be utilizd as one of the starting materials in the process of this invention include primary polyamines as in accordance with the set forth structure:

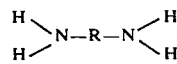

where R is an aryl, diaryl, diarylalkyl, or alkylaryl radical. Examples of suitable starting materials in accordance with the above promulgated structures include p-phenylenediamine, o-phenylenediamine, m-phenylenediamine, methyl-p-phenylenediamine, 2,4-diethyl-m-phenylenediamine, 1,5-naphthyldiamine, methylenedianiline, bis[4-( β-methylphenyl]methane, etc.

Suitable heterocyclic oxygen compounds would include but are not limited to tetrahydrofuran, 2-methyltetrahydrofuran, 2,5-dimethyltetrahydrofuran, tetrahydropyran, 2-methyltetrahydropyran, 2,6-dimethyltetrahydropyran, etc. It is understood that the aforementioned primary amines and heterocyclic oxygen compounds are only representative of the class of compounds which may be employed are not necessarily limited thereto.

It is contemplated within the scope of this invention that the mono- or di(heterocyclic nitrogen)-substituted diarylalkanes may be prepared in either a batch or continuous type of operation as known to one skilled in the art.

The following examples are given to illustrate the process of the present invention which, however, are not intended to limit the generally broad scope of the present invention in strict accordance therewith.

EXAMPLE I

In this example 4,4-bis-(N-pyrrolidinyl)diphenylmethane was prepared by the addition of 9.9 grams of mthylenedianiline to 70.6 grams of tetrahydrofuran in the presence of a catalyst comprising 1 percent iridium dispersed on an alumina support. The product was recovered, separated from the catalyst by filtration and analyzed by means of gas chromatography instrumentation which disclosed the presence of a mixture comprising 4-amino-4'-(N-pyrrolidinyl)diphenylmethane and 4,4'-bis-(N-pyrrolidinyl)diphenylmethane.

The 4,4'-bis-(N-pyrrolidinyl)diphenylmethane is separated by fractional crystallization from the 4-amino-4'-(N-pyrrolidinyl)-diphenylmethane, recovered and charged to an autoclave containing gasoline possessing a boiling point range of about 60°C. to about 200°C, said autoclave being equipped with a source of oxygen. The oxygen is charged according to the Induction Period analysis as set forth in ASTM test D-525 in which oxidation is shown to be prevented by the minimization of gum formation. A duplicate control sample without the addition of the 4,4'-bis(pyrrolidinyl)diphenylmethane is found to afford substantially less stability to oxygen than the sample treated with the 4,4'-bis(pyrrolidinyl)diphenylmethane.

EXAMPLE II

In this example the second part of the separated mixture of Example I, 4-amino-4'-(N-pyrrolidinyl)diphenylmethane is tested as set forth in the latter portion of Example I. The ASTM test No. D-525 indicates that the oxidation stability is improved by the presence of 4-amino-4'-(N-pyrrolidinyl)diphenylmethane.

EXAMPLE III

In this example 2,2-bis[4-(N-pyrrolidinyl)phenyl]propane is prepared by the reaction of 2,2-bis(4-aminophenyl)propane with tetrahydrofuran in the presence of a hydrogen chloride-alumina catalyst. The product is recovered and separated from the catalyst by filtration and analyzed by means of gas chromatography instrumentation which discloses the presence of 2,2-bis[4-(N-pyrrolidinyl)phenyl]propane.

The 2,2-bis[4-(N-pyrrolidinyl)phenyl]propane is charged to an autoclave containing kerosene possessing a boiling point of about 150°C to about 300°C, and subjected to an Induction Period analysis as set forth in ASTM test D-525 in which oxidation stability is improved as compared to a control sample which did not contain the additive.

EXAMPLE IV

In this example 2-methyl-4'-(N-piperidinyl)diphenylmethane is prepared by the addition of 2-methylmethylenedianiline to tetrahydropyran in the presence of a palladium dispersed on silica support catalyst. The product is recovered, separated from the catalyst by filtration and analyzed by means of gas chromatography instrumentation which discloses the presence of 2-methyl-4'-(N-piperidinyl)diphenylmethane.

The 2-methyl-4'-(N-piperidinyl)diphenylmethane is charged to an autoclave containing lubricating oil and tested for an Induction Period analysis as set forth in ASTM test D-525 in which the oxidation is shown to be retarded as compared to a control sample which does not contain the additive, 2-methyl-4'-(N-piperidinyl)-diphenylmethane.

We claim as our invention:

1. A petroleum distillate selected from the group consisting of gasoline, fuel oil, diesel oil, kerosene and lubricating oil, said distillate containing from 5 ppm to 200 ppm of a diphenylalkane having attached to at least one of the phenyl radicals a pyrrolidinyl or piperidinyl substituent.

2. The distillate of claim 1 further characterized in that the diphenylalkane has the formula

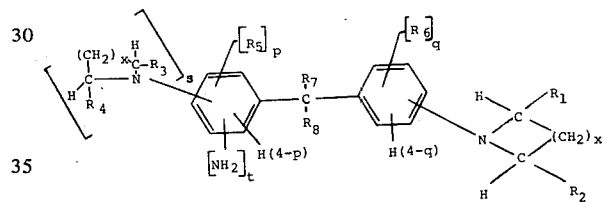

wherein $R_1 - R_8$ are selcted from a group consisting of methyl of hydrogen, $x$ is selected from the numbers 2 and 3, $s$ is selected from the numbers 0 or 1, $t$ is selected from the numbers 1 or 0 wherein, when $s$ is equal to 0, $t$ is equal to 1 and when $s$ is equal to 1, $t$ is equal to 0, and $p$ and $q$ are selected from the integers from 0 to 4.

3. The distillate of claim 1 further characterized in that said diphenylalkane is 4-amino-4'-(N-pyrrolidinyl)diphenylmethane.

4. The distillate of claim 1 further characterized in that said diphenylalkane is 2-amino-4'-(N-piperidinyl)-diphenylmethane.

5. The distillate of claim 1 further characterized in that said diphenylalkane is 4,4'-bis-(N-pyrrolidinyl)diphenylmethane.

6. The distillate of claim 1 further characterized in that said diphenylalkane is 4,4'-bis'(N-piperidinyl)diphenylmethane.

7. The distillate of claim 1 further characterized in that said diphenylalkane is 2,2'-bis[4-(N-pyrrolidinyl)-phenyl]propane.

8. The petroleum distillate of claim 1 being gasoline.

9. The petroleum distillate of claim 1 being kerosene.

10. The petroleum distillate of claim 1 being lubricating oil.

11. The petroleum distillate of claim 1 being fuel oil.

12. The petroleum distillate of claim 1 being diesel fuel.

* * * * *